United States Patent

Mayer et al.

Patent Number: 5,417,911
Date of Patent: May 23, 1995

[54] PROCESS FOR THE PREPARATION OF TETRASELENOTETRACENE HALIDES AND ELECTRICALLY CONDUCTIVE POLYMER COMPOSITIONS

[75] Inventors: Carl W. Mayer, Riehen; Ernst Minder, Sissach, both of Switzerland

[73] Assignee: Ciba-Geigy Corporation, Ardsley, N.Y.

[21] Appl. No.: 15,949

[22] Filed: Feb. 10, 1993

[30] Foreign Application Priority Data

Feb. 18, 1992 [CH] Switzerland .................. 472/92

[51] Int. Cl.$^6$ ............ C07D 517/02; B29C 41/24
[52] U.S. Cl. ................... 264/299; 264/104; 264/319; 540/1
[58] Field of Search ............ 264/104, 299; 540/1; 264/319

[56] References Cited

U.S. PATENT DOCUMENTS

| | | | |
|---|---|---|---|
| 4,601,853 | 7/1986 | Helti et al. | |
| 4,617,151 | 10/1986 | Mayer et al. | 540/1 |
| 4,801,701 | 1/1989 | Hilti et al. | 540/1 |
| 4,847,441 | 7/1989 | Helti et al. | 570/129 |
| 4,935,181 | 6/1990 | Theophilou et al. | 264/104 |

OTHER PUBLICATIONS

Chem. Absts. vol. 91, No. 21-91:175269a.
Chem. Physics Letters vol. 76, 1980 92-95.
Synthetic Metals, 41-43 (1991) pp. 951-954.

*Primary Examiner*—Mathieu D. Vargot
*Attorney, Agent, or Firm*—George R. Dohmann

[57] ABSTRACT

A process for the preparation of tetraselenotetracene chlorides or bromides of formula I,

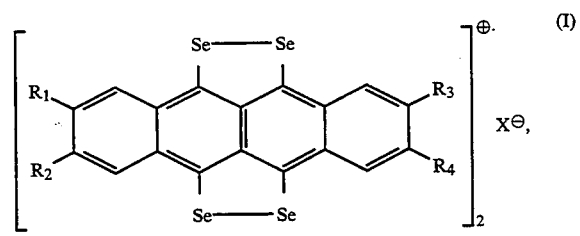

wherein $R_1$, $R_2$, $R_3$ and $R_4$ are each independently of one another H or F; $R_1$ is $CH_3$ and $R_2$, $R_3$ and $R_4$ are H; $R_1$, $R_2$, $R_3$ and $R_4$ are each $CH_3$; or $R_1$ and $R_2$ are $CH_3$ or Cl, and $R_3$ and $R_4$ are H, and X is Cl or Br, which process includes reacting a tetraselenotetracene of formula II

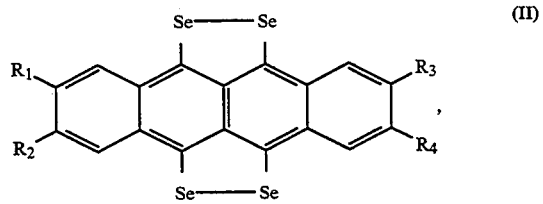

in a polar aprotic solvent, with stoichiometric amounts of an ammonium hydrochloride or hydrobromide, in the presence of oxygen at elevated temperature. An organic binder may be dissolved in the reaction solution and a substrate coated with this solution. After evaporation of the solvent, electrically conductive coatings are obtained that consist of a network of crystal needles of compounds of formula I in the binder matrix.

26 Claims, No Drawings

PROCESS FOR THE PREPARATION OF TETRASELENOTETRACENE HALIDES AND ELECTRICALLY CONDUCTIVE POLYMER COMPOSITIONS

The present invention relates to a process for the preparation of (tetraselenotetracene)₂ chlorides or (tetraselenotetracenes)₂ bromides by reacting tetraselenotetracene with oxygen and an ammonium hydrochloride or ammonium hydrobromide in the presence of a polar and aprotic solvent at elevated temperature. The solution may contain an organic binder so as to give, after evaporation of the solvent and any excess reactants and volatile reaction products, compositions that contain a (tetraselenotetracene)₂ chloride or (tetraselenotetracene)₂ bromide in the form of a network of crystal needles in the binder matrix.

In Synthetic Metals, 41–43, pages 951 to 954, J. Finter et al. describe the preparation of electrically conductive films of (tetraselenotetracene)₂ chloride in the form of a network of crystal needles in a polymer matrix by in situ crystallisation during the oxidation of tetraselenotetracene with e.g. hexachloropropene, in a solvent that contains the polymer, at elevated temperature and after evaporation of the solvent and any other volatile components. In the course of the reaction, substances form that corrode the metallic parts of processing machines such as rolls and conveyor belts, so that complicated and expensive protective measures are required. There is therefore a need to provide an oxidation process for the preparation of such films in which no corrosion of metallic parts is observed and by means of which conductive films of the same or even better quality can be obtained. The need also exists to provide a process for the preparation of tetraselenotetracene chlorides and bromides in which the reaction mixture induces no corrosion of metallic parts of the production plant.

Surprisingly, it has now been found that the oxidation of tetraselenotetracenes takes place in a polar and aprotic solvent with ammonium hydrochloride or hydrobromide and atmospheric oxygen, such that needle-shaped crystals form even in the presence of an organic binder. It has also surprisingly been found that the reaction mixture, despite the presence of halide, exerts no, or at most an insignificant, corrosive action on metallic parts of processing machines. The process is therefore particularly suitable for technical use and an economic production process.

Accordingly, the invention relates to a process for the preparation of tetraselenotetracene chlorides or bromides of formula I,

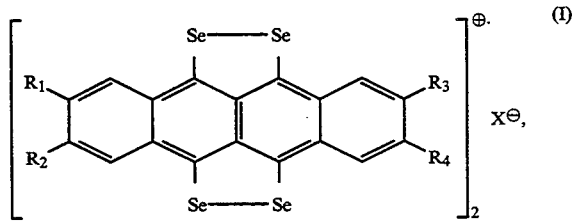

wherein $R_1$, $R_2$, $R_3$ and $R_4$ are each independently of one another H or F; $R_1$ is $CH_3$ and $R_2$, $R_3$ and $R_4$ are H; $R_1$, $R_2$, $R_3$ and $R_4$ are each $CH_3$; or $R_1$ and $R_2$ are $CH_3$ or Cl, and $R_3$ and $R_4$ are H, and X is Cl or Br, which process comprises reacting a tetraselenotetracene of formula II

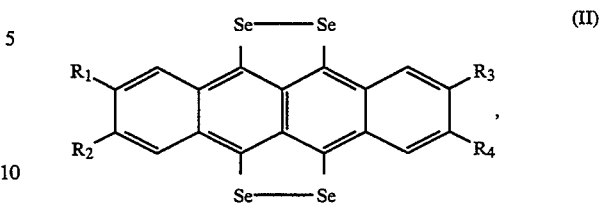

in a polar aprotic solvent, with stoichiometric amounts of an ammonium hydrochloride or hydrobromide, in the presence of oxygen at elevated temperature.

X in formula I is preferably Cl.

Preferred compounds of formula II are 2-fluorotetraselenotetracene, 2,3-difluorotetraselenotetracene, 2,3,8,9-tetrafluoro- or 2,3,8,9-tetramethyltetraselenotetracene and, most preferably, tetraselenotetracene.

Preferred inert solvents are N-alkylated acid amides and lactams. Representative examples of such solvents are tetramethylurea, hexamethylphosphoric triamide, dimethyl formamide, dimethyl acetamide and N-methylpyrrolidone. It is especially preferred to use N-methylpyrrolidone. The solvents conveniently contain minor amounts, typically 0.1 to 10% by weight, preferably 0.5 to 5% by weight, of water to enhance the solubility of the ammonium hydrohalides.

Stoichiometric amounts mean that at least ½ molar equivalent of an ammonium hydrochloride or hydrobromide and at least ½ molar equivalent of oxygen are used per 1 molar equivalent of a tetraselenotetracene. It is also possible to use an excess, conveniently up to a 10-fold excess, of the ammonium hydrochloride or hydrobromide.

The oxygen can be passed through the reaction solution in pure form as air or as a mixture of air with an inert gas, typically nitrogen, carbon dioxide, helium, neon or argon. In another embodiment of the process, it is possible to add to the reaction mixture oxygen donors, conveniently metal peroxides, hydrogen peroxide or inorganic peroxo salts. Typical examples of such oxidising agents are alkali metal peroxides such as sodium peroxide, and an alkali metal disulfate or ammonium disulfate, for example $Na_2S_2O_8$ or $(NH_4)_2S_2O_8$. It can be advantageous to use an oxygen donor in conjunction with pure gaseous oxygen or a mixture of oxygen with an inert gas. It is preferred to use pure oxygen, air or $H_2O_2$, or oxygen or air in conjunction with $H_2O_2$.

In a preferred embodiment of the process, hydrogen peroxide is further added to the reaction mixture to accelerate the reaction, conveniently in an amount of at least 20% of the amount of the ammonium hydrochloride or hydrobromide or up to a 10-fold excess. Normally 25% of the amount of ammonium hydrochloride or hydrobromide or up to a 10-fold excess will be used.

The reaction is preferably carried out in the temperature range from 40° to 250° C., more particularly from 70° to 200° C. and, most preferably, from 80° to 150° C.

Suitable ammonium hydrochlorides are typically pyridinium hydrochloride and those of formula $R_5R_6R_7N.HCl$, wherein $R_5$ is linear or branched $C_1$-$C_8$alkyl or $C_4$-$C_8$cycloalkyl, and $R_6$ and $R_7$ are each independently of the other H or have the meaning of $R_5$, or $R_5$ and $R_6$, when taken together, are tetramethylene, pentamethylene or 3-oxa-1,5-pentylene, and $R_7$ is H or has the meaning of $R_5$. Alkyl preferably contains 1 to 4, most preferably 1 or 2, carbon atoms. Especially preferred on account of the volatility of the resultant amines are hydrochlorides of formula $R_5R_6R_7N.HCl$, wherein $R_5$, $R_6$ and $R_7$ are $C_1$-$C_4$alkyl, preferably methyl or ethyl. The ammonium hydrobromides corresponding to these ammonium hydrochlorides are also suitable.

The inventive process may typically be carried out by dissolving a tetraselenotetracene in a solvent, with heating, conveniently in an inert gas atmosphere (typically nitrogen, helium, neon or argon), then adding a solution of the ammonium halide in the same solvent that contains a minor amount of water, and, if desired, adding simultaneously or separately an aqueous solution of hydrogen peroxide, then passing oxygen through the reaction mixture and carrying out the reaction under elevated temperature. The tetraselenotetracene halides are obtained as fine, black crystal needles which can be purified by conventional methods such as washing and drying. The tetraselenotetracene halides can be used as electrical conductors and incorporated into plastics materials as antistatic agents.

A particularly advantageous embodiment of the inventive process comprises dissolving an organic binder in the reaction solution, coating a substrate with this solution, and then evaporating the solvent at elevated temperature in the presence of oxygen (pure oxygen or a mixture of oxygen and an inert gas, including air) to form a layer on the substrate that contains a network of crystal needles of compounds of formula I in a matrix of the organic binder. The concurrent use of hydrogen peroxide is advantageous in this embodiment of the process. It is also advantageous to use ammonium hydrohalides of volatile amines to give coatings that are virtually free from reaction by-products. The preparation of the reaction solution and of the coating is best carried out in an inert gas atmosphere so as to prevent a premature formation of the tetraselenotetracene halides. Self-supporting films can be obtained by peeling the coating from the substrate or by known casting methods direct or continuously. In this variant of the process, the procedure comprises dissolving the polymer together with a tetracene of formula II in an inert solvent and then mixing the solution with the other reactants and afterwards coating a substrate.

Compared with the process disclosed in US-A-5 009 812 for the preparation of electrically conductive layers, films or foils containing a network of crystal needles of tetraselenotetracene halides in a synthetic polymer matrix, the process of this invention affords additional advantages to those described above. Very homogeneous layers with good conductivities in all directions are obtained, because the formation of the halides and their crystallisation substantially does not commence until after the coating has been carried out in an inert gas atmosphere when introducing oxygen, so that the alignment of crystal needles when coating can be avoided. Furthermore, the inventive process gives very fine-meshed needle networks which are mechanically more stable, so that films and foils may be rolled without loss of electrical conductivity. In the coating methods, no deposit of crystals is observed in the mixer unit or in the jet or spray nozzle, so that interruptions can be substantially avoided during production.

The amounts of tetraselenotetracene and binder in the reaction solution is conveniently chosen such that, after evaporation of the solvent, the coating contains 0.01 to 10% by weight, preferably 0.3 to 5% by weight, of tetraselenotetracene halide of formula I and 99.9 to 90% by weight, preferably 99.7 to 95% by weight, of binder.

The binders are preferably natural or synthetic polymers. Suitable polymers are typically thermosetting, thermoplastic or structurally crosslinked polymers. The thermoplastic polymers may conveniently be selected from the following polymers, copolymers or mixtures of these polymers:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$-$C_9$) including hydrogenated modifications thereof (e.g. tackifiers) and mixtures of polyalkylenes and starch.

5. Polystyrene, poly(p-methylstyrene), poly($\alpha$-methylstyrene).

6. Copolymers of styrene or $\alpha$-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/-butylene/styrene or styrene/ethylene/-propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.
8. Halogen-containing polymers such as polychloroprene, chlorinated rubbers, chlorinated or sulfochlorinated polyethylene, copolymers of ethylene and chlorinated ethylene, epi-chlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.
9. Polymers derived from α,β-unsaturated acids and derivatives thereof such as polyacrylates and polymethacrylates; polymethyl methacrylates, polyacrylamides and polyacrylonitriles, impact-modified with butyl acrylate.
10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.
11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.
12. Homopolymers and copolymers of cyclic ethers such as polyalkylene glycols, polyethylene oxide, polypropylene oxide or copolymers thereof with bisglycidyl ethers.
13. Polyacetals such as polyoxymethylene and those polyoxymethylenes which contain ethylene oxide as a comonomer, polyacetals modified with thermoplastic polyurethanes, acrylates or MBS.
14. Polyphenylene oxides and sulfides, and mixtures of polyphenylene oxides with styrene polymers or polyamides.
15. Polyurethanes derived from hydroxyl-terminated polyethers, polyesters or polybutadienes on the one hand and aliphatic or aromatic polyisocyanates on the other, as well as precursors thereof.
16. Polyamides and copolyamides derived from diamines and dicarboxylic acids and/or from amino-carboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).
17. Polyureas, polyimides, polyamide-imides and polybenzimidazoles.
18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.
19. Polycarbonates and polyester carbonates.
20. Polysulfones, polyether sulfones and polyether ketones.
21. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
22. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.
23. Polyethers of diglycidyl compounds, typically diglycidyl ethers and diols, for example of a diglycidyl ether of bisphenol A and bisphenol A.

Preferred thermoplastic polymers are polyolefins, polystyrene, polyvinyl chloride, polyvinylidene chloride, polyvinylidene fluoride, polyacrylates, polymethacrylates, polyamides, polyesters, polycarbonates, polysulfones, polyethers, polyether sulfones, polyimides and polyvinyl carbazole.

The thermosetting and structurally crosslinked polymers may be typically the following polymers:

1. Crosslinked polymers which are derived from aldehydes on the one hand and phenols, ureas and melamines on the other hand, such as phenol/formaldehyde resins, urea/formaldehyde resins and melamine/formaldehyde resins.
2. Drying and non-drying alkyd resins.
3. Unsaturated polyester resins which are derived from copolyesters of saturated and unsaturated dicarboxylic acids with polyhydric alcohols and vinyl compounds as crosslinking agents, and also halogen-containing modifications thereof of low flammability.

4. Crosslinkable acrylic resins derived from substituted acrylic esters such as epoxy acrylates, urethane acrylates or polyester acrylates.
5. Alkyd resins, polyester resins or acrylate resins which are cross-linked with melamine resins, urea resins, polyisocyanates or epoxy resins.
6. Rubber derived from crosslinked polydienes, for example butadiene or isoprene; silicon rubber.
7. Epoxy resins which are derived from polyepoxides, for example from bisglycidyl ethers or from cycloaliphatic diepoxides, and which may contain a hardener as crosslinking agent or which are crosslinked thermally using curing accelerators or by irradiation.

Among the crosslinked polymers, crosslinked epoxy resins are preferred which, as polyepoxides, are derived preferably from glycidyl compounds which contain on average two epoxy groups in the molecule. Particularly suitable glycidyl compounds are those which contain two glycidyl groups, $\beta$-methylglycidyl groups or 2,3-epoxycyclopentyl groups attached to a hetero atom (e.g. sulfur, preferably oxygen or nitrogen), in particular bis(2,3-epoxycyclopentyl) ether; diglycidyl ethers of polyhydric aliphatic alcohols, such as 1,4-butanediol, or polyalkylene glycols, such as polypropylene glycols; diglycidyl ethers of cycloaliphatic polyols, such as 2,2-bis(4-hydroxycyclohexyl)propane; diglycidyl ethers of polyhydric phenols, such as resorcinol, bis(p-hydroxyphenyl)methane, 2,2-bis-(p-hydroxyphenyl)propane (=diomethane), 2,2-bis(4'-hydroxy-3',5'-dibromophenyl)propane, 1,3-bis(p-hydroxyphenyl)ethane; bis($\beta$-methylglycidyl) ethers of the above dihydric alcohols or dihydric phenols; diglycidyl esters of dicarboxylic acids, such as phthalic acid, terephthalic acid, $\Delta_4$-tetrahydrophthalic acid and hexahydrophthalic acid; N,N-diglycidyl derivatives of primary amines and amides and heterocyclic nitrogen bases which contain two N-atoms, and N,N'-diglycidyl derivatives of disecundary diamides and diamines, such as N,N-diglycidylaniline, N,N-diglycidyltoluidine, N,N-diglycidyl-p-aminophenyl methyl ether, N,N'-dimethyl-N,N'-diglycidylbis(p-aminophenyl)methane; N',N''-diglycidyl-N-phenyl-isocyanurate; N,N'-diglycidyl ethyleneurea; N,N'-diglycidyl-5,5-dimethylhydantoin, N,N'-diglycidyl-5-isopropyl-hydantoin, N,N-methylenebis(N',N'-diglycidyl-5,5-dimethylhydantoin), 1,3- bis(N-glycidyl-5,5-dimethylhydantoin)2-hydroxypropane; N,N'-diglycidyl-5,5-dimethyl-6-isopropyl-5,6-dihydrouracil, triglycidyl isocyanurate.

A preferred group of epoxy resins comprises glycidylated novolaks, hydantoins, aminophenols, bisphenols and aromatic diamines or cycloaliphatic epoxy compounds. Particularly preferred epoxy resins are glycidylated cresol novolaks, bisphenol A and bisphenol F diglycidyl ether, hydantoin-N,N'-bisglycide, p-aminophenol triglycide, diaminodiphenylmethane tetraglycide, vinylcyclohexene dioxide, 3,4-epoxycyclohexylmethyl-3,4-epoxycyclohexanecarboxylate or mixtures thereof.

Further suitable epoxy resins are prereacted adducts of such epoxy compounds with epoxy hardeners, for example an adduct of a diglycidyl ether of bisphenol A and bisphenol A, or adducts which have been prereacted with oligoesters which carry two terminal carboxyl groups and epoxides.

Suitable hardeners for epoxy resins are acid or basic compounds. Illustrative examples of suitable hardeners are: polyhydric phenols (resorcinol, 2,2-bis(4-hydroxyphenyl)propane) or phenol-formaldehyde resins; polybasic carboxylic acids and the anhydrides thereof, such as phthalic anhydride, tetrahydrophthalic anhydride, hexahydrophthalic anhydride, 4-methylhexahydrophthalic anhydride, 3,6-endomethylene-tetrahydrophthalic anhydride, 4-methyl-3,6-endomethylen-tetrahydrophthalic anhydride (methylnadic anhydride), 3,4,5,6,7,7-hexachloroendomethylene-tetrahydrophthalic anhydride, succinic anhydride, adipic anhydride, trimethyladipic anhydride, sebacic anhydride, maleic anhydride, dodecylsuccinic anhydride, pyromellitic dianhydride, trimellitic anhydride, benzophenonetetracarboxylic dianhydride, or mixtures of such anhydrides.

A preferred group of hardeners comprises novolaks and polycarboxylic anhydrides.

The epoxy resins can also be additionally cured with curing accelerators or only with thermal curing catalysts. Exemplary of curing accelerators and catalysts are 3-ethyl-4-methylimidazole, triamylammonium phenolate; mono- or polyphenols (phenol, diomethane, salicylic acid); boron trifluoride and the complexes thereof with organic compounds, such as boron trifluoride ether complexes and boron trifluoride amine complexes ($BF_3$/monoethylamine complex); phosphoric acid and triphenylphosphite.

Curing accelerators and catalysts are normally added in an amount of 0.1 to 10% by weight, based on the epoxy resin. Hardeners for epoxy resins are normally used in equimolar amounts, based on the epoxy groups and functional groups of a hardener.

Further additives for enhancing processing properties, the mechanical, electrical and thermal properties, surface properties and light stability can be blended into the polymers. Exemplary of such additives are finely particulate fillers, reinforcing fillers, plasticisers, lubricants and mould release agents, adhesion promoters, antistatic agents, antioxidants, heat and light stabilisers, pigments and dyes.

A preferred embodiment of the polymers prepared according to the process of this invention and which contain a tetraselenotetracene halide (hereinafter referred to as compositions) comprises those polymers that are shaped to mouldings, films, foils, fibres, or to coatings on at least one surface of a substrate.

In a particularly preferred embodiment of the invention, the novel composition is in the form of a film or foil or a coating on at least one surface of a substrate. Such embodiments are conveniently prepared by dissolving or suspending a thermoplastic polymer or at least one starting material of a thermosetting polymer or a structurally crosslinked polymer in an inert solvent and then mixing the solution or suspension with the reaction mixture, and subsequently applying the composition by known coating techniques to a substrate which may be preheated, and thereafter removing the solvent by heating and while passing in oxygen, and crosslinkable compositions can then additionally be fully cured. Self-supporting films and foils are obtained by peeling the coating from the substrate or by coating techniques, typically curtain coating.

Examples of suitable substrates are glass, metals, plastics, mineral and ceramic materials, wood and paper. The substrates may be of any external shape and are typically mouldings, filaments, fibres, fabrics, bars, pipes, ribbons, sheets, boards, rolls or casings.

Suitable coating techniques are typically brushing, rolling, doctor coating, casting, spin coating, curtain coating and spraying. Doctor coating, casting and spraying are especially preferred coating techniques.

Suitable inert solvents for polymers and starting materials for polymers are typically polar and, preferably, aprotic solvents, which may be used singly or in mixtures of at least two solvents. Representative examples of such solvents are: ethers (dibutyl ether, tetrahydrofuran, dioxane, ethylene glycol monomethyl or dimethyl ether, ethylene glycol monoethyl or diethyl ether, diethylene glycol diethyl ether, triethylene glycol dimethyl ether), halogenated hydrocarbons (methylene chloride, chloroform, 1,2-dichloroethane, 1,1,1-trichloroethane, 1,1,2,2-tetrachloroethane), carboxylates and lactones (ethyl acetate, methyl propionate, ethyl benzoate, 2-methoxyethyl acetate, γ-butyrolactone, δ-valerolactone, pivalolactone), carboxamides and lactams (N,N-dimethylformamide, N,N-diethylformamide, N,N-dimethylacetamide, tetramethylurea, hexamethylphosphoric triamide, γ-butyrolactam, ε-caprolactam, N-methylpyrrolidone, N-acetylpyrrolidone, N-methylcaprolactam), sulfoxides (dimethyl sulfoxide), sulfones (dimethyl sulfone, diethyl sulfone, trimethylene sulfone, tetramethylene sulfone), tertiary amines (N-methylpiperidine, N-methylmorpholine) substituted benzenes (benzonitrile, chlorobenzene, o-dichlorobenzene, 1,2,4-trichlorobenzene, nitrobenzene, toluene, xylene) and nitriles (acetonitrile, propionitrile), and ketones such as acetone and methyl butyl ketone.

For carrying out the inventive process in the presence of polymers or starting materials of thermosetting polymers or structurally crosslinked polymers it may be convenient to use mixtures of solvents, preferably mixtures of the above solvents with N-alkylated acid amides and lactams.

The coating techniques can conveniently be carried out by dissolving the individual components separately and combining them just before application of the chosen technique. However, it is also possible to prepare two solutions of the components, for example solvent, polymer and tetraselenotetracene or ammonium hydrohalide as well as solvent, ammonium hydrohalide and tetraselenotetracene, or to combine all the components in one solution.

The solutions are preferably heated, conveniently to 40°-250° C. It is useful to heat the substrate as well to accelerate the removal of the solvent, which is normally effected in the temperature range from 50° to 250° C., more preferably 70° to 200° C. and, most preferably, from 80° to 150° C., until the coating is dry. If it is desired to detach the coatings to give self-supporting films or sheets, the substrate can be treated with antiblocking agents prior to coating.

It is also possible to produce pure layers of networks of crystal needles of the CT complexes on a substrate by applying to a substrate solutions or suspensions of the CT complexes in a solvent and afterwards evaporating the solvent. Such layers can be electrochemically metallised to enhance the conductivity, conveniently with Cu, Pt or Pd. It can be useful to provide such pure layers with a protective coating of a polymer.

The layer thicknesses can vary over a wide range, depending on the choice of coating method. Spray methods give very thin layers, whereas thicker layers can also be obtained with brushing and casting methods. The layer thicknesses can be typically from 0.01 to 5000 μm, preferably from 0.1 to 1000 μm and, most preferably, from 0.1 to 500 μm.

Depending on the choice of polymer, the novel compositions are opaque or transparent and have outstanding electrical properties. Thus, surprisingly, the coatings and mouldings have an excellent discharge capacity which, for heterogeneous materials, is otherwise difficult to achieve or cannot be achieved at all. The compositions are therefore especially suitable for use for making antistatically treated moulded pans for the electrostatic screening of components or for making antistatically treated mouldings. The high conductivities also permit the use of the novel compositions as electric conductors, for example as electrodes for display elements or electronic components as well as charge carriers in capacitors. The compositions also have excellent mechanical strength and performance properties.

The following Examples illustrate the invention in more detail.

A) Preparation of the Tetraselenotetracene Halides

Example A1: Preparation of (tetraselenotetracene)$_2$Cl.

200 mg (0.3704 mmol) of tetraselenotetracene are dissolved in 120 ml of N-methylpyrrolidone (NMP) at 140° C. in a sulfonating flask under a stream of argon and with stirring. The solution is cooled to 95° C. and then 1.77 ml of a solution of NMP containing 1% of trimethylammonium hydrochloride (0.1852 mmol) and 2% of water as well as 0.105 ml of 3% aqueous hydrogen peroxide (0.0926 mmol) are added. Afterwards the stream of argon is replaced by a stream of oxygen and the reaction mixture is stirred for 1.5 hours at 100° C. The title compound precipitates in the form of fine, black crystal needles. After cooling to room temperature, the black precipitate is isolated by filtration, washed with NMP and acetone and then dried at 50° C. under a high vacuum, giving 152.5 mg (75%)of (tetraselenotetracene)$_2$Cl which has a specific resistance $\sigma = 24 \, \Omega^{-1}.cm^{-1}$ (crystal powder measurement).

Example A2: Preparation of (tetraselenotetracene)$_2$Cl.

9.80 g of tetraselenotetracene are dissolved at 144° C. in 6000 g of N-methylpyrrolidone. The NMP is continuously fed at 72 ml/min from the feed vessel into a mixing chamber and there mixed with 1.67 ml/min of a solution of N-methylpyrrolidone containing 0.7% of trimethylamine hydrochloride and 2% of hydrogen peroxide (30%). The reaction mixture is cooled to room temperature. The resultant (tetraselenotetracene)$_2$ chloride crystals are isolated by filtration and dried at 100° C. and 0. 1 mbar. The yield is 7.8 g. The isolated crystals are identified as (tetraselenotetracene)$_2$ chloride by X-ray powder analysis.

Example A3: Preparation of (2-fluorotetraselenotetracene)$_2$Cl.

66.8 mg of 2-fluorotetraselenotetracene are dissolved at 140° C. After 30 minutes the bath temperature is lowered over 10 minutes to 100° C. Then 600 μl of a solution of N-methylpyrrolidone containing 1% of trimethylammonium hydrochloride and 2% of water are added and the mixture is thereafter mixed with 120 μl of a 3% solution of hydrogen peroxide in N-methylpyrrolidone. Air is passed through the reaction mixture while cooling, whereupon crystals precipitate. The crystal needles are isolated by filtration at room temperature and then dried for 4 hours at 100° C. and 0.1 mbar, giving 54.4 mg of crystal needles having a length of 50–100 μm. These crystals are electrically conductive. The isolated compound is identified as (2-fluorotetraselenotetracene)₂Cl by X-ray powder analysis.

B) Use Examples

Example B1: Preparation of an electrically conductive polycarbonate film.

30 mg of tetraselenotetracene and 2.5 g of polycarbonate are dissolved at 150° C. in 14.5 g of NMP. After about 30 minutes 300 μl of a solution of NMP containing 1% of trimethylammonium hydrochloride and 1% of water are added and the mixture so obtained is subsequently mixed with 3 μl of 30% aqueous hydrogen peroxide. The hot mixture is applied to a glass plate with a doctor blade (wet film thickness about 270 μm) and the solvent is evaporated at 110° C. to give a transparent polycarbonate film that contains a dense network of crystal needles of (tetraselenotetracene)₂Cl and which has a layer thickness of about 24 μm. The conductivity is 0.15 S/cm.

Example B2: Preparation of an electrically conductive polycarbonate film 30 mg of tetraselenotetracene and 2.5 g of polycarbonate are dissolved at 150° C. in 14.5 g of NMP. After about 30 minutes 300 μl of a solution of NMP containing 1% of trimethylammonium hydrochloride, 1% of water, 1% of H₂O₂ and 5% of polycarbonate are added and the components are mixed. The hot mixture is applied to a glass plate with a doctor blade (wet film thickness about 270 μm) and the solvent is evaporated at 110° C. to give a transparent polycarbonate film that contains a dense network of crystal needles of (tetraselenotetracene)₂Cl and which has a layer thickness of about 22 μm. The conductivity is 0.08 S/cm.

Example B3: Preparation of an electrically conductive polycarbonate film 18.1 mg of tetraselenotetracene and 0.9 g of polycarbonate are dissolved at 150° C. in 24 g of NMP. After about 1 hour, 180 μl of a solution of NMP containing 1% of trimethylammonium hydrochloride and 1% of water and then 10 μl of a 3% aqueous solution of H₂O₂ are added and the components are subsequently mixed. The mixture is then sprayed on to a glass plate (spray conditions: two-fluid steel nozzle, propellant argon, spraying rate 4 cm/s, distance from nozzle to glass plate c. 20 cm) and the solvent is evaporated at 110° C., giving a transparent polycarbonate film that contains a dense network of crystal needles of (tetraselenotetracene)₂Cl and which has a layer thickness of about 5 μm. The conductivity is 0.77 S/cm.

Example 4: Preparation of an electrically conductive polyether film 44.18 mg of tetraselenotetracene and 3.0 g of a polyether (polyadduct of a diglycidyl ether of bisphenol A and bisphenol A) are dissolved at 150° C. in 48 g of NMP. After about 45 minutes, 400 μl of a solution of NMP containing 1% of trimethylammonium hydrochloride and 2% of water are added, followed by the addition of 300 μl of a 3% solution of H₂O₂ in NMP/water (9:1), and the components are mixed by stirring. The mixture is sprayed on to a glass plate (spray conditions: two-fluid steel nozzle, propellant argon, spraying rate 4 cm/s, distance from nozzle to glass plate c. 20 cm) and the solvent is evaporated at 100° C., giving a transparent polyether film that contains a dense network of crystal needles of (tetraselenotetracene)₂Cl and which has a layer thickness of about 5 μm. The conductivity is 1 S/cm.

Example B5: Preparation of an electrically conductive polyether imide film 40 mg of tetraselenotetracene and 4.0 g of polyether imide are dissolved in 20 g of N-methylpyrrolidone at 155° C. Then 660 μl of a solution of N-methylpyrrolidon containing 0.8% of trimethylammonium hydrobromide, 1.6% of hydrogen peroxide (30%) and 2% of water are added and the components are mixed. The hot mixture is applied with a doctor blade to a preheated glass plate (wet film thickness c. 250 μm) and the solvent is evaporated at 120° C., giving a transparent polyether imide film that contains an electrically conductive network of crystal needles of (tetraselenotetracene)₂ chloride and which has a layer thickness of c. 20 μm. The conductivity is 0.1 S/cm.

Example B6: Preparation of an electrically conductive polycarbonate film 33.2 mg of tetraselenotetracene and 2.5 g of polycarbonate are dissolved at 150° C. in 17.5 g of NMP. After about 50 minutes 450 μl of a solution of NMP containing 1% of trimethylammonium hydrobromide and 2% of water are added and the components are subsequently mixed with 40 μl of a 3% solution of hydrogen peroxide in N-methylpyrrolidone. The hot mixture is coated on to a glass plate with a doctor blade (wet film thickness about 270 μm) and the solvent is evaporated at 110° C. to give a dense, electrically conductive network of crystal needles of (tetraselenotetracene)₂ bromide and which has a layer thickness of about 20 μm. The conductivity is 0.2 S/cm.

Example B7: Preparation of an electrically conductive polyether film 13.6 mg of tetraselenotetracene and 1.5 g of a polyether (polyadduct of a diglycidyl ether of bisphenol A and bisphenol A) are dissolved at 150° C. in 25 g of NMP. After about 1 hour, 140 μl of a solution of NMP containing 1% of trimethylammonium hydrochloride and 1% of water are added, followed by the addition of 50 μl of a 3% solution of H₂O₂ in NMP and the components are mixed by stirring. The mixture is sprayed on to each of a p-and n-doped silicon wafer (spray conditions: two-fluid steel nozzle, propellant argon, spraying rate 4 cm/s, distance from nozzle to wafer c. 20 cm) and the solvent is evaporated at 100° C., giving on each wafer a transparent polyether film that contains a dense network of crystal needles of (tetraselenotetracene)₂ chloride and which has a layer thickness of about 7 μm.

What is claimed is:

1. A process for the preparation of a tetraselenotetracene chloride or bromide of formula I

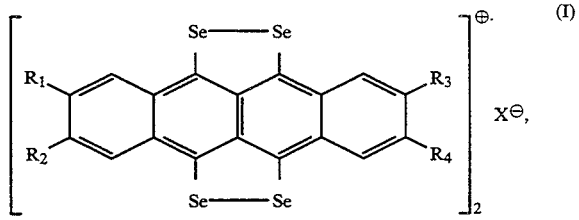

wherein $R_1$, $R_2$, $R_3$ and $R_4$ are each independently of one another H or F; or $R_1$ is $CH_3$ and $R_2$, $R_3$, $R_4$ are H; or $R_1$, $R_2$, $R_3$ and $R_4$ are each $CH_3$; or $R_1$ and $R_2$ are $CH_3$ or Cl, and $R_3$ $R_4$ are H, and X is Cl or Br, which process comprises reacting a tetraselenotetracene of formula II

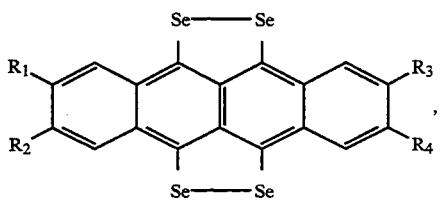

(II)

in a polar aprotic solvent, with stoichiometric amounts of an ammonium hydrochloride or hydrobromide, in the presence of an effective oxidizing amount of oxygen or an oxygen donor, or a combination thereof, at elevated temperature.

2. A process according to claim 1, wherein X in formula I is Cl.

3. A process according to claim 1, wherein the compound of formula II is selected from the group consisting of 2-fluorotetraselenotetracene, 2,3-difluorotetraselenotetracene, 2,3,8,9-tetrafluoro- or 2,3,8,9-tetramethyltetraselenotetracene and tetraselenotetracene.

4. A process according to claim 3, wherein the compound of formula II is tetraselenotetracene.

5. A process according to claim 1, wherein the solvent is an N-alkylated acid amide or a lactam.

6. A process according to claim 1, wherein the solvent is N-methylpyrrolidone.

7. A process according to claim 1, wherein at least ½ molar equivalent of an ammonium hydrochloride or hydrobromide and at least ½ molar equivalent of oxygen are used per 1 molar equivalent of a tetraselenotetracene.

8. A process according to claim 1, wherein the reaction is carried out in the temperature range from 40° to 250° C.

9. A process according to claim 8, wherein the reaction is carried out in the temperature range from 70° to 200° C.

10. A process according to claim 8, wherein the reaction is carried out in the temperature range from 80° to 150° C.

11. A process according to claim 1, wherein the ammonium hydrochloride or hydrobromide is selected from the group consisting of pyridinium hydrochloride and hydrochlorides of formula $R_5R_6R_7N \cdot HCl$, wherein $R_5$ is linear or branched $C_1$-$C_8$alkyl or $C_4$-$C_8$cycloalkyl, and $R_6$ and $R_7$ are each independently of the other H or have the meaning of $R_5$, or $R_5$ and $R_6$, when taken together, are tetramethylene, pentamethylene or 3-oxa-1,5-pentylene, and $R_7$ is H or has the meaning of $R_5$, and the corresponding hydrobromides.

12. A process according to claim 11, wherein the alkyl contains 1 to 4 carbon atoms.

13. A process according to claim 11, wherein the hydrochlorides are those of formula $R_5R_6R_7N \cdot HCl$, wherein $R_5$, $R_6$ and $R_7$ are $C_1$-$C_4$alkyl.

14. A process according to claim 11, wherein $R_5$, $R_6$ and $R_7$ are methyl or ethyl.

15. A process according to claim 1, which comprises dissolving an organic binder in the aprotic solvent to form a reaction solution, coating a substrate with the reaction solution, and then evaporating the solvent at an elevated temperature in the presence of an effective oxidizing amount of oxygen to form a layer on the substrate that contains a network of crystal needles of (tetraselenotetracene)$_2$ chloride or (tetraselenotetracene)$_2$ bromide in a matrix of the organic binder.

16. A process according to claim 15, wherein the reaction solution additionally contains hydrogen peroxide.

17. A process according to claim 15, wherein the amount of tetraselenotetracene and binder in the reaction solution is such that, after evaporation of the solvent, the coating contains 0.01 to 10% of tetraselenotetracene halide of formula I and 99.9 to 90% of binder.

18. A process according to claim 15, wherein the preparation of the reaction solution and of the coating is carried out in an inert gas atmosphere.

19. A process according to claim 15 wherein the binder is a thermoplastic polymer or a starting material of a thermosetting or structurally crosslinked polymer which, after coating, is hardened or crosslinked.

20. A process according to claim 19, wherein the thermoplastic polymer is selected from the group consisting of polyolefins, polystyrene, polyvinyl chloride, polyvinylidene chloride, polyvinylidene fluoride, polyacrylates, polymethacrylates, polyamides, polyesters, polycarbonates, polysulfones, polyethers, polyether sulfones, polyimides and polyvinyl carbazole.

21. A process according to claim 15, wherein the layer for the preparation of a film or foil is peeled from the substrate.

22. A process according to claim 21, which is carried out continuously as a casting method.

23. A process according to claim 1 wherein the oxygen is present in the form of pure oxygen or air.

24. A process according to claim 1 wherein hydrogen peroxide is the oxygen donor.

25. A process according to claim 1 wherein the oxygen donor is a combination of oxygen and hydrogen peroxide.

26. A process according to claim 24 wherein the amount of hydrogen peroxide is from 20 percent to a ten-fold excess relative to the mount of the ammonium hydrochloride or ammonium hydrobromide.

* * * * *